(12) United States Patent
Clarence-Smith

(10) Patent No.: US 11,389,420 B2
(45) Date of Patent: *Jul. 19, 2022

(54) PHARMACEUTICAL COMPOSITIONS AND METHODS UTILIZING NEOSTIGMINE AND AN NK-1 ANTAGONIST FOR TREATING MYASTHENIA GRAVIS

(71) Applicant: DAS-MG, Inc., Boston, MA (US)

(72) Inventor: Kathleen Clarence-Smith, Washington, DC (US)

(73) Assignee: DAS-MG, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/752,591

(22) Filed: Jan. 24, 2020

(65) Prior Publication Data
US 2020/0155495 A1    May 21, 2020

Related U.S. Application Data

(63) Continuation of application No. PCT/US2018/043391, filed on Jul. 24, 2018.

(60) Provisional application No. 62/695,497, filed on Jul. 9, 2018, provisional application No. 62/536,680, filed on Jul. 25, 2017.

(51) Int. Cl.
*A61K 31/24* (2006.01)
*A61P 21/04* (2006.01)
*A61K 31/5377* (2006.01)

(52) U.S. Cl.
CPC .......... *A61K 31/24* (2013.01); *A61K 31/5377* (2013.01); *A61P 21/04* (2018.01)

(58) Field of Classification Search
CPC ...................................................... A61K 31/24
USPC ...................................................... 514/236.2
See application file for complete search history.

(56) References Cited

U.S. PATENT DOCUMENTS

| 4,042,698 | A | 8/1977 | Zappia | |
|---|---|---|---|---|
| 9,782,397 | B2 * | 10/2017 | Ferrari | A61K 31/4545 |
| 2009/0264388 | A1 * | 10/2009 | Maghni | A61K 45/06 |
| | | | | 514/171 |
| 2011/0243924 | A1 | 10/2011 | Supervia | |

FOREIGN PATENT DOCUMENTS

| CN | 102258492 | A | * | 5/2010 | ............... A61K 9/22 |
|---|---|---|---|---|---|
| CN | 102552381 | | * | 7/2011 | ........... A61K 36/481 |
| CN | 102552381 | | | 7/2012 | |
| CN | 102258492 | | | 12/2012 | |
| CN | 105708838 | | | 6/2016 | |
| CN | 102552381 | | * | 10/2017 | ........... A61K 36/481 |
| JP | 56104814 | | | 8/1981 | |
| RU | 2010130899 | | | 1/2012 | |
| WO | 2006005017 | | | 1/2006 | |

OTHER PUBLICATIONS

Gillies, Proceedings of the Australian Association of Neurologists, 1978, vol. 14(Clin. Exp. Neurol. 1977), p. 271-279.*
Couturier, Journal of the American Veterinary Medical Association (2009), 235(12), 1462-6.*
Lorenz, Journal of the American Veterinary Medical Association. , 1972, vol. 161(7), p. 795-800.*
Langford, Core Evid. 2010; 5: 77-90.*
Wolff, Burger's medicinal Chemistry and Drug Discovery, vol. 1, Principles and Practice, John Wiley & sons, New York, 1997.*
West, Solid State Chemistry and Its Applications, john Wiley & Sons, 1984.*
Gold et al. Therapeutic Advances in Neurological Disorders, 2008; 1 (2):99-114.
Langford, et al., Fosaprepitant and aprepitant: an update of the evidence for their place in the prevention of chemotherapy induced nausea and vomiting, Core Evidence, Sep. 24, 2009 (Sep. 24, 2009), vol. 5, pp. 77-90.
International Search report for PCT/US2018/43391 dated Oct. 2, 2018.
Abicht A, Muller J S, Lochmiiller H. Congenital Myasthenic Syndromes. In: Pagon RA, Adam MP, Ardinger HH, Wallace SE, Amemiya A, Bean LJH, Bird TD, Ledbetter N, Mefford HC, Smith RJH, Stephens K, editors. GeneReviews® [Internet]. Seattle (WA): University of Washington, Seattle; 1993-2016. May 9, 2003 [updated Jul. 14, 2016].
Cho J-R, Duong AV, Nguyen LTT, Chi S-C. "Design of transdermal matrix patch containing ondansetron". J Pharm Investigation. 2016 46(7): 677-684.
Drachman DB. Myasthenia Gravis. Semin Neurol. 2016; 36:419-424. Epub Sep. 23, 2016.
Engel AG. Congenital Myasthenic Syndromes in 2012. Curr. Neurol Neurosci Rep, 2012; 12(1):92-101.
Gotterer L, Li Y. Maintenance immunosuppression in myasthenia gravis. J Neurol Sci. 2016; 369:294-302. Epub Aug. 28, 2016.
Howard J.F. Clinical Overview of MG. Myasthenia Gravis Foundation of America; 2015.
Koland M et al. 2010: Koland M, Sandeep VP. Charyulu NR. Fast Dissolving Sublingual Films of Ondansetron Hydrochloride: Effect of Additives on in vitro Drug Release and Mucosal Permeation. J Young Pharmacists. 2010, 2(3):216-222.
O'Grady GL, Verschuuren C, Yuen M, Webster R, Menezes M, Fock JM, Pride N, Best HA, Benavides Damm T, Turner C, Lek M, Engel AG, North KN, Clarke NF, MacArthur DG, Kamsteeg EJ, Cooper ST. Variants in SLC18A3, vesicular acetylcholine transporter, cause congenital myasthenic syndrome. Neurology. 2016; 87:1442-1448. Epub Sep. 2, 2016.

(Continued)

Primary Examiner — Nizal S Chandrakumar
(74) Attorney, Agent, or Firm — Transformative Legal, LLC; Len S. Smith; Julie E. Kurzrok

(57) ABSTRACT

The present invention describes the use of a NK1-antagonist, in constant combination with neostigmine, to facilitate the treatment of a patient suffering from myasthenia gravis by providing a therapeutically effective neostigmine bromide or methylsulfate daily dose without the dose-limiting gastrointestinal adverse effects.

19 Claims, No Drawings

(56) References Cited

OTHER PUBLICATIONS

Phillips WD, Vincent A. Pathogenesis of myasthenia gravis: update on disease types, models, and mechanisms. FI000Research 2016, 5(F1000 Faculty Rev): 1513 updated Jun. 27, 2016.
Shelton GD. Myasthenia gravis and congenital myasthenic syndromes in dogs and cats: A history and mini-review. Neuromuscul Disord. 2016; 26: 331-334. Epub Mar. 10, 2016.
Smith SV, Lee AG. Update on Ocular Myasthenia Gravis. Neurol Clin. 2017; 35:115-123.
Myasthenia Gravis Fact Sheet; National Institute of neurological Discorders and Stroke, 2017.
Makarious et al, "Myasthenia gravis: An Emerging Toxicity of Immune Checkpoint Inhibitors", European Journal of Cancer 82(2017) 128-136, Jun. 27, 2017.
Bloxiverz Prescribing Information, Revised May 2013.

* cited by examiner

PHARMACEUTICAL COMPOSITIONS AND METHODS UTILIZING NEOSTIGMINE AND AN NK-1 ANTAGONIST FOR TREATING MYASTHENIA GRAVIS

RELATED APPLICATIONS

This application is a continuation of PCT/US2018/043391 (published as WO/2019/023175), filed Jul. 24, 2018, and claims the benefit of U.S. Provisional Patent Application Ser. No. 62/536,680, filed on 25 Jul. 2017, and of U.S. Provisional Patent Application Ser. No. 62/695,497, filed 9 Jul. 2018, the disclosures of which are incorporated herein in their entirety by reference.

FIELD OF THE INVENTION

This invention pertains to the field of the treatment of myasthenia gravis and other myasthenic syndromes in patients suffering from this disease. The invention describes new compositions, methods, and combinations for safely treating myasthenia gravis.

OBJECTS OF THE INVENTION

The present invention provides new compositions, methods, and combinations to enable the safe administration of neostigmine to mammalian subjects with myasthenic syndromes, including myasthenia gravis, which comprise administering to a patient in need of said treatment an effective daily dose of a NK1-antagonist in combination with an effective daily dose of a pharmaceutically acceptable salt of neostigmine.

DEFINITIONS

"MG": Myasthenia Gravis. MG is a chronic neuromuscular autoimmune disease, characterized by muscle weakness. The basic abnormality in MG is a reduction in the acetylcholine nicotinic receptors (AChRs) at neuromuscular junctions due to the effects of autoantibodies. About 85% of patients with generalized MG have antibodies to AChRs. Antibodies to other proteins at the neuromuscular junction are present in some cases of MG, such as antibodies to muscle-specific kinase, or to low density lipo-protein 4, or to agrin.

"Myasthenic syndrome": refers to conditions associated with muscle weakness in which the cholinergic transmission at the neuromuscular junction is decreased either because of a decrease in the number and/or dysfunction of post-synaptic nicotinic receptors or to a decrease in the amount of acetylcholine ("Ach") available at the neuromuscular junction due to gene mutations in the presynaptic proteins involved in the synthesis, storage and release of ACh, or to degeneration of cholinergic nerves that innervate muscles. An emerging myasthenic syndrome (with or without auto antibodies to nicotinic receptors) has been reported in association with immune-therapies used for the treatment of certain malignancies. Myasthenic syndromes are sometimes loosely referred to as MG in the medical literature but herein, all MG-like conditions which do not involve autoantibodies to nicotinic receptors will be referred to as myasthenic syndromes. MG itself is a myasthenic syndrome and is considered as such herein, although, as the most prominent myasthenic syndrome it is often mentioned specifically (as in the phrase "MG and other myasthenic syndromes").

"NK1-antagonist": an antagonist of the neurokinin receptor subtype-1, in the literature also referred to as NK1 receptor antagonist or NK1 receptor inhibitor.

"Effective daily dose of NK1-antagonist": as used herein, refers to a daily dose of said NK1-antagonist of from 1 µg to 600 mg.

"Neostigmine": unless otherwise specified, this term, as used herein, refers to a pharmaceutically acceptable salt of neostigmine ("neostigmine pharmaceutically acceptable salt"), the daily doses and the amounts per unit form thereof being expressed as equivalents of neostigmine bromide per oral unit forms, and equivalents of neostigmine methylsulfate per injectable unit forms.

"Effective daily dose of neostigmine": this expression, as used herein, refers to a neostigmine pharmaceutically acceptable salt daily dose, including doses used in the titration period, equivalent to at least 15 mg of neostigmine bromide administered orally or to at least 0.5 mg of neostigmine methylsulfate administered parenterally.

"Maximally effective (daily) dose" or "Maximal effective (daily) dose", as used herein for neostigmine, refers to any neostigmine daily dose allowing the expression of significantly greater neostigmine efficacy, heretofore hindered by the typical gastro-intestinal neostigmine adverse effects.

"Effective amount per unit form", referring to neostigmine, is a neostigmine amount per unit form equivalent to at least 0.2 mg of neostigmine methylsulfate in a parenteral 1 ml-solution unit form or as released from a transdermal drug delivery system; or a neostigmine amount per unit form equivalent to at least 15 mg of neostigmine bromide in an oral unit form.

"Neostigmine bromide" or "neostigmine methylsulfate": these expressions, or equivalent ones, as used herein in connection with neostigmine doses, refer to a neostigmine dose per unit form or to a neostigmine daily dose (range) equivalent to either neostigmine bromide, in the case of an oral dose, or to neostigmine methylsulfate, in the case of a parenteral dose.

"Mammal" or "mammalian subject" as used herein refers to any class of warmblooded higher vertebrates (such as placentals, marsupials, or monotremes) that nourish their young with milk secreted by mammary glands, have the skin usually more or less covered with hair; and include, but are not limited to, a human, a dog, and a cat.

BACKGROUND OF THE INVENTION

Myasthenia gravis (MG) is a chronic autoimmune disease of the neuromuscular junction (NMJ) caused by antibodies that attack components of the postsynaptic membrane, impair neuromuscular transmission, and lead to varying degrees of weakness and fatigue of skeletal muscle. The prevalence of MG in the United States is estimated at 14 to 20 per 100,000 population, with approximately 36,000 to 60,000 cases in the United States (Howard, 2015). However, MG remains underdiagnosed and the prevalence is probably higher. The disease has also been described in dogs, and cats (Shelton, 2016).

The hallmark of the disease is muscle weakness that increases during periods of activity and improves after periods of rest. Muscular weakness can be generalized or localized to certain muscle groups, and involvement of the bulbar and respiratory muscles can be life threatening (Phillips and Vincent, 2016). Groups of muscles are often involved in typical patterns. Certain muscles such as those that control eye and eyelid movement, facial expression, chewing, talking, and swallowing are often, but not always, involved in the disorder. The muscles that control breathing and neck and limb movements may also be affected.

MG occurs in all ethnic groups and both genders. It most commonly affects young adult women (under 40) and older men (over 60), but it can occur at any age (Myasthenia Gravis Fact Sheet; National Institute of Neurological Disorders and Stroke, 2016). In neonatal myasthenia, the fetus may acquire immune proteins (antibodies) from a mother affected with myasthenia gravis. Generally, cases of neonatal MG are temporary and the child's symptoms usually disappear within 2-3 months after birth (Myasthenia Gravis Fact Sheet; National Institute of Neurological Disorders and Stroke, 2016). Other children develop MG indistinguishable from adults. MG in juveniles is uncommon (Myasthenia Gravis Fact Sheet; National Institute of neurological Disorders and Stroke, 2016).

The basic abnormality in MG is a reduction in acetylcholine receptors (AChRs) at neuromuscular junctions due to the effects of autoantibodies that are directed against the AChRs in most patients, or against neighboring proteins involved in the clustering of AChRs, such as MuSK, LRP-4, or agrin (Drachman, 2016).

The diagnosis may be missed during the early stages of the disease, and depends on the recognition of clinical manifestations, the measurement of autoantibodies, and/or electrophysiological features (Drachman, 2016).

Rarely, children may show signs of congenital myasthenia or congenital myasthenic syndrome (CMS). These are not autoimmune disorders, but are caused by defective genes that produce abnormal proteins instead of those that normally are involved in cholinergic transmission: acetylcholinesterase (the enzyme that breaks down acetylcholine), acetylcholine receptors, and other proteins present along the muscle membrane (Engel, 2012).

In some rare cases, a myasthenic syndrome is due to bi-allelic variants in the gene encoding the vesicular acetylcholine transporter (VAChT) located in the presynaptic terminal (O'Grady et al, 2016).). In other cases, degeneration of the nerves that innervate muscles such as occurs with aging (Lexell, 1997) leads to a myasthenic syndrome. Recently (Makarious et al, 2017), have reported on a myasthenic syndrome involving an emerging toxicity of checkpoint inhibitors used for the treatment of certain malignancies. Most individuals with CMS, or with an immune-oncology therapy-related myasthenic syndrome, or with progressive age-related degeneration of the motor neurons that innervate muscles, benefit from the same treatment as those that are effective in patients with autoimmune MG, namely choline esterase (ChE) inhibitors (Engel 2012; Abicht et al, 2003 updated in 2014).

Ocular myasthenia gravis (OMG) is a localized form of myasthenia gravis in which autoantibodies directed against acetylcholine receptors block or destroy these receptors at the postsynaptic neuromuscular junction. The hallmark of OMG is a history of painless weakness or fatigability of the extraocular muscles and ptosis with normal pupillary function and visual acuity. Clinical, laboratory, electrophysiologic, and pharmacologic tests are available for diagnosis. Treatment can begin with symptom management; there is no cure (Smith and Lee, 2017).

The treatment of myasthenic syndromes involves treatment of the symptoms through the enhancement of cholinergic transmission at the neuromuscular junction by acetylcholine esterase inhibitors (AChEIs) that do not appreciably cross the Blood-Brain-Barrier (BBB), such as neostigmine. Patients with autoimmune-related myasthenic syndromes may also benefit from immunotherapy to slow disease progression. Options for immunosuppression include corticosteroids, azathioprine, mycophenolate mofetil, cyclosporine, tacrolimus, methotrexate, rituximab, cyclophosphamide, intravenous immunoglobulin, plasmapheresis, and thymectomy (Gotterer and Li, 2016).

Neostigmine treats the symptoms by retarding the enzymatic hydrolysis of acetylcholine at cholinergic synapses, so that acetylcholine concentrations increase at the neuromuscular junction and the effect of acetylcholine is both increased and prolonged. Cholinesterase inhibitors have been shown to cause considerable improvement in some patients and little to none in others (Howard, 2015). Strength rarely returns to normal, possibly because of dose-limiting adverse events (diarrhea, nausea, vomiting) that preclude the use of maximally effective doses of neostigmine.

Neostigmine bromide (Prostigmin®), iodide or methylsulfate, all of which do not appreciably cross the BBB, are commonly used for the treatment of MG. No fixed dosage schedule suits all patients. Neostigmine is commercially available as a brand or generic drug, for example as oral Prostigmin, consisting of tablets comprising 15 mg neostigmine bromide and vials for parenteral injection comprising 0.5 mg of neostigmine methylsulfate, a 15 mg of neostigmine bromide oral dose being equivalent to a 0.5 mg of neostigmine methylsulfate parenteral dose.

A neostigmine bromide slow release preparation which can be taken once every day for treating myasthenia gravis is described in CN 102258492, the contents of which are incorporated herein in their entirety by reference.

Neostigmine is also described in combination with some plant extracts according to traditional Chinese medicine (CN 102552381), for treating myasthenia gravis.

A process for the synthesis of neostigmine iodide and neostigmine methylsulfate is disclosed in RU 2010130899, the contents of which are incorporated herein in their entirety by reference.

Neostigmine methylsulfate has been disclosed as a remedy for eye diseases, in an eye drop preparation, consisting of a neostigmine methylsulfate aqueous solution, also containing other chemicals, emulsified with an oily higher fatty acid solution obtained from olive oil and isopropyl myristate (JPS 56104814, the contents of which are incorporated herein in their entirety by reference).

Neostigmine methylsulfate has also been disclosed, in combination with naphazoline hydrochloride and chlorpheniramine maleate, for the treatment of conjunctivitis (CN 105708838, the contents of which are incorporated herein in their entirety by reference).

The need for neostigmine varies from day-to-day and during the same day in response to infection, menstruation, emotional stress, and hot weather. Gastro-intestinal adverse effects of neostigmine used to treat MG are dose-limiting and typically consist of gastrointestinal complaints, queasiness, loose stools, nausea, vomiting, abdominal cramps, and diarrhea (Howard, 2015).

Gastro-intestinal side effects are an important source of discomfort for the patient, may be a source of non-compliance, or may result in the need to decrease the daily dose of neostigmine to mitigate these side effects whereupon these side effects become dose-limiting. As a consequence, efficacy is reduced.

Normally, said gastro-intestinal side effects, in particular when using neostigmine methylsulfate intravenous injection (0.5 mg/ml vials or 1 mg/ml in 10-ml multiple dose vials), are counteracted by a previous or concurrent administration of glycopyrrolate as recommended in the label for injectable neostigmine (Bloxyverz Prescribing Information, revised May 2013).

However, the literature does not disclose how to safely treat MG with neostigmine by increasing the neostigmine doses without the undesired gastrointestinal dose-limiting adverse effects that are inevitably associated to said treatment, thus creating the possibility of an improvement of the condition of patients suffering from this disabling disease.

Thus, the problem of providing tolerable, safe, chronic treatment of MG and other myasthenic syndromes with neostigmine at high, maximally effective doses remains unsolved.

SUMMARY OF THE INVENTION

It has now been found that, by using a neurokinin-1 receptor antagonist, also referred to as NK1 receptor inhibitor or simply NK1-antagonist, in constant combination with neostigmine, it is possible to treat symptoms of muscle weakness associated with MG and other myasthenic syndromes in mammalian subjects, and particularly humans, dogs, and cats, suffering from myasthenia gravis and other myasthenic syndromes, by maintaining a therapeutically effective neostigmine bromide daily dose or a therapeutically effective neostigmine methylsulfate daily dose with little to no dose-limiting gastro-intestinal adverse effect.

In particular, the constant combination of a NK1-antagonist with neostigmine enables for the first time greater or complete efficacy of neostigmine in the treatment of symptoms of muscle weakness associated with MG and other myasthenic syndromes.

Thus, the present invention provides a method for treating symptoms of muscle weakness associated with MG and other myasthenic syndromes, which comprises administering to a mammalian subject in need of said treatment a combination of a NK1-antagonist with an effective dose of neostigmine.

Any of the NK1-antagonists disclosed in the literature may be used, in the present invention, in combination with a dose of neostigmine that is generally at least as high as that of the neostigmine bromide or neostigmine methylsulfate currently used doses for treating MG, and even much higher. The chronic use of this combination mitigates or even eliminates the gastro-intestinal dose-limiting adverse effects of neostigmine, thus enabling the safe administration of the recommended or even higher than currently recommended dose of neostigmine (maximally effective dose), leading to greater efficacy and safety of neostigmine.

According to the present invention, preferably, the NK1-antagonists used are those shown to be effective for preventing or treating nausea and vomiting following cancer chemotherapy. In fact, surprisingly, NK1-antagonists, known to block nausea, vomiting, and diarrhea induced by chemotherapeutic drugs, have been shown, in particular when administered at high doses, to also block the gastro-intestinal side effects of neostigmine without affecting its efficacy in treating symptoms of muscle weakness associated with MG or other myasthenic syndromes, thus allowing the administration of neostigmine maximally effective doses.

This finding is surprising also because, notwithstanding the gravity of the illness and the fact that both neostigmine and the NK1-antagonists were two families of products in use during more than a decade, each in its own indication, to date nobody thought that, by combining an effective dose of NK1-antagonist with an effective dose of neostigmine, it would have been possible to safely improve the conditions of patients suffering from MG and other myasthenic syndromes.

Thus, the present invention provides a method for treating symptoms of muscle weakness associated with MG and other myasthenic syndromes, which comprises administering to mammalian subjects, and in particular, humans, dogs, and cats, in need of said treatment an effective daily dose of a NK1-antagonist in combination with an effective daily dose of a pharmaceutically acceptable salt of neostigmine.

According to an embodiment, the invention provides a pharmaceutical combination comprising a NK1-antagonist, at a daily dose that is at least as high as the pediatric or adult dose shown to be effective for the prevention or treatment of chemotherapy-induced nausea and vomiting, and a maximally effective dose of a neostigmine pharmaceutically acceptable salt.

According to another embodiment, the invention provides a NK1-antagonist, in a pharmaceutical composition comprising, as an active ingredient, said NK1-antagonist in an amount at least as high as the pediatric or adult dose shown to be effective for the prevention or treatment of chemotherapy-induced nausea and vomiting, in admixture with a pharmaceutical carrier, for use for preventing or attenuating the dose-limiting gastrointestinal adverse effects of neostigmine in the treatment of symptoms of muscle weakness associated with MG and other myasthenic syndromes in a mammalian subject in need of said treatment.

According to a further embodiment, the invention includes the use of a NK1-antagonist for the preparation of a medicament including a pharmaceutical composition comprising, as an active ingredient, said NK1-antagonist, in an amount per unit form at least as high as the pediatric or adult dose shown to be effective for the prevention or treatment of chemotherapy-induced nausea and vomiting (effective amount per unit form), in admixture with a pharmaceutical carrier, for attenuating or even abrogating the gastrointestinal adverse effects of neostigmine in the treatment of symptoms of muscle weakness associated with MG and other myasthenic syndromes, in a mammalian subject in need of said treatment.

As set forth above, the amount per unit form of the NK1-antagonist is at least as high as the pediatric or adult dose shown to be effective for the prevention or treatment of chemotherapy-induced nausea and vomiting and may be up to 4 times and even up to 6 times said dose.

Said composition comprising said NK1-antagonist for the first time allows the safe administration of currently used effective doses and also higher, maximally effective neostigmine doses to mammalian subjects suffering from symptoms of muscle weakness associated with MG or other myasthenic syndromes, with the consequent expression of the neostigmine greater efficacy.

In particular, said composition comprising said NK1-antagonist allows the safe administration of oral neostigmine daily, maximally effective dose equivalent to from 375 mg to 1500 mg, of neostigmine bromide; and parenteral, normally subcutaneous, maximally effective infusion over 24 hours ("24 h-infusion") neostigmine doses equivalent to from 10 mg to 500 mg of neostigmine methylsulfate.

According to yet a further embodiment, the invention provides a pharmaceutical fixed-dose combination including a pharmaceutical composition in dosage unit form comprising a NK1-antagonist, in an amount per unit form that is at least as high as the pediatric or adult dose shown to be effective for the prevention and treatment of chemotherapy-induced nausea and vomiting, as Component (a) and an effective amount per unit form of a neostigmine pharmaceutically acceptable salt, as Component (b), in admixture with a pharmaceutical carrier or vehicle.

According to a preferred embodiment, the invention provides a pharmaceutical combination comprising an approved NK1-antagonist, at a dose that is at least as high as the pediatric or adult dose approved for the prevention or treatment of chemotherapy-induced nausea and vomiting, and an effective, especially maximally effective, dose of a neostigmine pharmaceutically acceptable salt.

According to an aspect of this preferred embodiment, the invention provides an approved NK1-antagonist, in a pharmaceutical composition comprising, as an active ingredient, said NK1-antagonist in an amount at least as high as the pediatric or adult dose approved for the prevention or treatment of chemotherapy-induced nausea and vomiting, in admixture with a pharmaceutical carrier, for use for preventing, attenuating or even abrogating the gastrointestinal adverse effects of neostigmine in the treatment of myasthenia gravis and other myasthenic syndromes.

According to a further aspect of this preferred embodiment, the invention includes the use of an approved NK1-antagonist for the preparation of a medicament consisting of a pharmaceutical composition comprising, as an active ingredient, said NK1-antagonist, in an amount at least as high as the pediatric or adult dose approved for the prevention or treatment of chemotherapy-induced nausea and vomiting, in admixture with a pharmaceutical carrier, for preventing, attenuating or even abrogating the gastrointestinal adverse effects of neostigmine in the treatment of myasthenia gravis and other myasthenic syndromes.

According to yet a further aspect of this preferred embodiment, the invention provides a pharmaceutical fixed-dose combination comprising a pharmaceutical composition comprising a NK1-antagonist, in an amount per unit form that is at least as high as the pediatric or adult dose approved for the prevention and treatment of chemotherapy-induced nausea and vomiting, as Component (a) and an effective amount per unit form of a neostigmine pharmaceutically acceptable salt, as Component (b), in admixture with a pharmaceutical carrier or vehicle.

As set forth above, the amount of the NK1-antagonist is at least as high as the pediatric or adult dose approved for the prevention or treatment of chemotherapy-induced nausea and vomiting and may be up to 6 times said dose.

Among the approved NK1-antagonists to be used in combination, including fixed-dose combinations, with neostigmine, aprepitant and pharmaceutically acceptable salts and solvates and prodrugs thereof, rolapitant and pharmaceutically acceptable salts and solvates thereof, and netupitant and pharmaceutically acceptable salts and solvates and prodrugs thereof are particularly advantageous.

In the above combination, including fixed-dose combinations, said amount per unit form of said NK1-antagonist Component (a) in said composition normally is from 1 µg to 600 mg. The NK1-antagonist daily dose is from 1 µg to 600 mg.

In the above combination, including fixed-dose combinations, the neostigmine Component (b) amount, per unit form including any administration route and titration, is equivalent to from 0.03 mg to 500 mg of neostigmine bromide or methylsulfate. The neostigmine daily dose, including any administration route and titration, is equivalent to from 0.2 mg to 1500 mg of neostigmine bromide or neostigmine methylsulfate.

The unit dose of neostigmine is equivalent to a range of from 0.09 mg to 500 mg of neostigmine bromide or methylsulfate, including unit doses (in the case of multidose systems) and unit forms, for their use in the titration period.

The neostigmine oral dose per unit form, in an IR tablet, will be in a range equivalent to from 1 mg to 200 mg, preferably from 17.5 mg to 200 mg, normally from 15 mg to 75 mg or from 17.5 mg to 75 mg of neostigmine bromide, depending on safety and tolerability, in combination with a NK1-antagonist. Per day the dose, in neostigmine bromide, is from 0.5 mg to 1500 mg, normally from 15 mg to 1200 mg, from 15 mg to 450 mg or from 15 mg to 375 mg, in combination with a NK1-antagonist.

If the NK1-antagonist is aprepitant or a pharmaceutically acceptable salt thereof, its dose per IR unit form, will correspond to from 10 mg to 125 mg of aprepitant, in combination with neostigmine. If the NK1-antagonist is rolapitant, the dose/unit form in combination with neostigmine at the above doses/unit form, will range from 15 mg to 270 mg in an IR formulation.

The effective or maximally effective dose of neostigmine, normally as methylsulfate, administered by intravenous injection, is at least 0.03 mg/kg to 0.07 mg/kg administered as an intravenous bolus, the recommended maximum total dose normally being at least 5 mg.

The present invention further provides a kit or package comprising a pharmaceutical combination or pharmaceutical or veterinary composition as described herein, and instructions for use of the same for treatment of a MG and other myasthenic syndromes in a patient in need thereof.

DETAILED DESCRIPTION

The present invention improves the conditions of mammalian subjects suffering from MG and other myasthenic syndromes by chronic treatment with neostigmine and a NK1-antagonist to said patient.

In particular, the present invention provides, according to certain aspects, a method for safely improving the conditions or symptoms of muscle weakness associated with of mammalian subjects, particularly, humans, dogs, and cats, suffering from MG or other myasthenic syndromes by treating said subjects with a NK1-antagonist in combination with neostigmine;

a NK1-antagonist, for use in the treatment of MG and other myasthenic syndromes in combination with neostigmine;

the use of a NK1-antagonist for the preparation of a medicament for the treatment of symptoms of muscle weakness associated with MG and other myasthenic syndromes in combination with neostigmine; and a fixed-dose combination consisting of a pharmaceutical composition in dosage unit form comprising, as active ingredients, a NK1-antagonist Component (a) and neostigmine Component (b).

The present invention also relates to the use of a NK1-antagonist for the preparation of a medicament for the treatment of symptoms of muscle weakness associated with MG and other myasthenic syndromes, said medicament being a pharmaceutical composition in dosage unit form comprising, as an active ingredient, said NK1-antagonist Component (a), and, as a second active ingredient, said neostigmine Component (b), in admixture with a pharmaceutically acceptable carrier or vehicle.

The NK1-antagonist Component (a)

Any NK1-antagonist may be used for providing the safe treatment of MG and other myasthenic syndromes with normal but also with high and very high maximally effective doses of neostigmine. Antagonists of the NK1 receptor that are shown to be effective for the prevention or treatment of chemotherapy-induced nausea and vomiting are particularly useful according to the present invention.

The NK1-antagonist is preferably selected from the group consisting of

5-[[(2R,3S)-2-[(1R)-1-[3,5-bis(trifluoromethyl)phenyl] ethoxy]-3-(4-fluorophenyl)-4-morpholinyl]methyl]-1,2-dihydro-3H-1,2,4-triazol-3-one (aprepitant); described in U.S. Pat. No. 5,719,147, and in a liquid oral formulation, in US 2017/0035774, and in an injectable emulsion in a single-dose vial for intravenous use containing 130 mg aprepitant in 18 ml of emulsion (Cinvanti®), described in U.S. Pat. No. 9,808,465 (the contents of each disclosure is incorporated herein in its entirety by reference);

[3-{[(2R,3S)-2-[(1R)-1-[3,5-bis(trifluoromethyl)phenyl] ethoxy]-3-(4-fluorophenyl)morpholin-4-yl]methyl}-5-oxo-2H-1,2,4-triazol-1-yl]phosphonic acid (fosaprepitant), disclosed, for example as dimeglumine salt in in U.S. Pat. No. 5,691,336 and as di(cyclohexylamine) salt in US 2016/355533 (the contents of each disclosure are incorporated herein in their entirety by reference);

(2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide (casopitant) described in U.S. Pat. No. 7,294,630 (the contents of each disclosure are incorporated herein in their entirety by reference);

(2S)-1-[(3aS,4S,7aS)-4-hydroxy-4-(2-methoxyphenyl)-7,7-diphenyl-1,3,3a,5,6,7a-hexahydroisoindol-2-yl]-2-(2-methoxyphenyl)propan-1-one (INN: dapitant);

(2S,3S)—N-(5-tert-Butyl-2-methoxybenzyl)-2-(diphenylmethyl)-1-azabicyclo[2.2.2]octan-3-amine (maropitant, disclosed in U.S. Pat. No. 5,807,867, WO2005/082416 and EP 3173071) (the contents of each disclosure are incorporated herein in their entirety by reference);

(2S,3S)-2-Diphenylmethyl-3-[(5-isopropyl-2 methoxybenzyl)amino]quinuclidine (ezlopitant), disclosed by Evangelista S (2001). "Ezlopitant. Pfizer"; Current Opinion in Investigational Drugs: 2 (10): 1441-3; reviewed in Drugs: the Investigational Drugs Journal 6 (8): 758-72 (the contents of each disclosure are incorporated herein in their entirety by reference);

(2S)—N-{2-[3,5-bis(trifluoromethyl)phenyl]ethyl}-2-[4-(cyclopropylmethyl)piperazin-1-yl]-N-methyl-2-phenylacetamide (INN figopitant);

N-[(2R)-1-[Acetyl-[(2-methoxyphenyl)methyl] amino]-3-(1H-indol-3-yl)propan-2-yl]-2-(4-piperidin-1-ylpiperidin-1-yl)acetamide (lanepitant);

2-[3,5-bis(trifluoromethyl)phenyl]-N,2-dimethyl-N-[4-(2-methylphenyl)-6-(4-methyl-1-piperazinyl)-3-pyridinyl] propanamide (netupitant) described in U.S. Pat. Nos. 6,297,375, 6,719,996 and 6,593,472, and, in an oral composition, comprising 300 mg of netupitant and palonosetron hydrochloride in an amount equivalent to 0.5 mg of palonosetron base, herein below referred to as "netupitant-300/palonosetron'-0.5, described in U.S. Pat. No. 8,951,969 (the contents of each disclosure are incorporated herein in their entirety by reference);

{4-[5-{2-[3,5-bis(trifluoromethyl)phenyl]-N,2-dimethyl-propanamido}-4-(2-methylphenyl)pyridin-2-yl]-1-methylpiperazin-1-ium-1-yl}methyl hydrogen phosphate (INN: fosnetupitant), described in WO 2013/082102 and, in a pure crystalline form, in US 2017/0096442, available in an injectable composition, comprising 235 mg of fosnetupitant and palonosetron hydrochloride in an amount equivalent to 0.25 mg of palonosetron base (Akynzeo® for injection), herein below referred to as "netupitant-235palonosetron-0.25" (the contents of each disclosure are incorporated herein in their entirety by reference);

(2R,4S)-4-[(8aS)-6-oxo-1,3,4,7,8,8a-hexahydropyrrolo[1,2-a]pyrazin-2-yl]-N-[(1R)-1-[3,5-bis(trifluoromethyl)phenyl]ethyl]-2-(4-fluoro-2-methylphenyl)-N-methylpiperidine-1-carboxamide (orvepitant);

(5S,8S)-8-({(1R)-1-[3,5-bis(trifluoromethyl)phenyl] ethoxy}methyl)-8-phenyl-1,7-diazaspiro[4.5]decan-2-one (rolapitant), described in U.S. Pat. No. 7,049,320 and, for an injectable form thereof, in U.S. Pat. No. 9,101,615 (the contents of each disclosure are incorporated herein in their entirety by reference);

3-((3aR,4R,5S,7aS)-5-[(1R)-1-[3,5-bis(trifluoromethylphenyl]ethoxy]-4-(4-fluorophenyl)-1,3,3a,4,5,6,7,7a-octahydroisoindol-2-ylcyclopent-2-en-1-one (serlopitant) described in U.S. Pat. Nos. 7,544,815 and 7,217,731 (the contents of each disclosure are incorporated herein in their entirety by reference);

2-(S)-(4-Fluoro-2-methyl-phenyl)-piperazine-1-carboxylic acid [1-(R)-(3,5-bis-trifluoromethyl-phenyl)-ethyl]-methyl-amide (vestipitant), described in WO 2001/25219 and, in intravenous formulation having a reduced tendency to cause hemolysis, in WO 2012/175434 (the contents of each disclosure are incorporated herein in their entirety by reference); and (2S,3S)—N-[(2-methoxy-5-[5-(trifluoromethyl)tetrazol-1-yl]phenylmethyl]-2-phenylpiperidin-3-amine (GR2015171, vofopitant), described in U.S. Pat. No. 5,703,240 (see also U.S. Pat. No. 8,093,268) and also disclosed by Gardner C J et al. RegulPept. 1996 Aug. 27; 65(1):45-53 (the contents of each disclosure are incorporated herein in their entirety by reference).

Preferably, said NK1-antagonist is selected from the group consisting of aprepitant and pharmaceutically acceptable salts, solvates and prodrugs thereof.

Illustrative examples of pharmaceutically acceptable salts of basic advantageous NK1-antagonists include acid addition salts with mineral or organic acids such as hydrochloric acid, hydrobromic acid, hydriodic acid, sulfuric acid, sulfamic acid, nitric acid, carbonic acid, phosphoric acid, formic acid, acetic acid, propionic acid, stearic acid, oxalic acid, malonic acid, succinic acid, fumaric acid, maleic acid, hydroxymaleic acid, lactic acid, malic acid, tartaric acid, citric acid, ascorbic acid, phenylacetic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, aspartic acid, glutamic acid and pamoic (embonic) acid. Said salt may be solvated with a solvent, said solvent normally being water.

Illustrative examples of pharmaceutically acceptable salts of acidic NK1-antagonists such as fosaprepitant include salts with inorganic bases such as alkaline metal or alkaline-earth metal salts, and salts with organic bases such as dicyclohexylamine salts, N-methyl-D-glucamine (meglumine) salts, and salts with amino acids, as described in U.S. Pat. No. 5,691,336, the contents of which is incorporated herein in its entirety by reference. Aprepitant, fosaprepitant meglumine, fosaprepitant di(cyclohexylamine), rolapitant, rolapitant hydrochloride, netupitant-300/palonosetron-0.5 and fosnetupitant-235/palonosetron-0.25 are particularly advantageous NK1-antagonists.

Fosaprepitant, fosaprepitant meglumine, and fosaprepitant di(cyclohexylamine), are prodrugs of aprepitant, and fosnetupitant is a prodrug of netupitant. Thus, the expressions "fosaprepitant and pharmaceutically acceptable salts and solvates and prodrugs thereof and "netupitant and pharmaceutically acceptable salts and solvates and prodrugs thereof include aprepitant, fosaprepitant, fosaprepitant meglumine, fosaprepitant di(cyclohexylamine), and, respectively, netupitant and fosnetupitant.

Antagonists of the NK1 receptor that are approved for the prevention or treatment of postoperative nausea and vomiting or for the prevention of chemotherapy-induced nausea and vomiting are particularly useful according to the present invention. In particular, aprepitant is commercially available (Emend®) in capsules containing 40 mg, 80 mg, or 125 mg aprepitant, in one 150-mg powder in single-dose glass vial, for reconstitution for intravenous injection, or, as fosaprepitant dimeglumine (Emend® Injection, Ivemend®), in vials containing 115 mg or 150 mg fosaprepitant; rolapitant is available (Varubi®) in 90-mg tablets; and netupitant-300/palonostron-0.5, available (Akynzeo®) in a fixed-dose combination in capsules containing 300 mg of netupitant and 0.5 mg of the NK1-antagonist palonosetron (as hydrochloride); and fosnetupitant-235/palonosetron-0.25 mg, available (Akynzeo® for injection) in single-dose vial for reconstitution for intravenous injection, are particularly advantageous NK1-antagonists.

Aprepitant and pharmaceutically acceptable salts and solvates and prodrugs thereof; rolapitant and pharmaceutically acceptable salts and solvates thereof; and netupitant and pharmaceutically acceptable salts and solvates and prodrugs thereof are particularly advantageous NK1-antagonists in the combination of the present invention.

More particularly, in said combination, said NK1-antagonist is selected from the group consisting of aprepitant and pharmaceutically acceptable salts and solvates thereof, at a daily dose equivalent to from 10 mg to 250 mg of aprepitant; fosaprepitant and pharmaceutically acceptable salts and solvates thereof, at a daily dose equivalent to from 10 mg to 250 mg of aprepitant; rolapitant and pharmaceutically acceptable salts and solvates thereof, at a daily dose equivalent to from 15 mg to 270 mg of rolapitant, netupitant and pharmaceutically acceptable salts and solvates thereof, at a daily dose equivalent to from 300 mg to 600 mg; netupitant-300/palonosetron-0.5 once a day; and fosnetupitant-235/palonosetron-0.25 once a day.

For its administration to a patient suffering from MG or a myasthenic syndrome, in combination with neostigmine, each of the above NK1-antagonists is formulated in a pharmaceutical composition in dosage unit form comprising, as an active ingredient, said NK1-antagonist, in admixture with a pharmaceutical carrier or vehicle.

In particular, said NK1-antagonist active ingredient of said pharmaceutical composition is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg of netupitant; fosnetupitant and pharmaceutically acceptable salts and solvates thereof; netupitant-300/palonosetron-0.5; and fosnetupitant-235/palonosetron-0.25.

Advantageously, said NK1-antagonist is aprepitant, in an amount per unit form of from 10 mg to 250 mg; fosaprepitant meglumine, in an amount per unit form equivalent to from 10 mg to 250 mg of aprepitant; or rolapitant, in an amount per unit form of from 15 mg to 270 mg or from 30 mg to 270 mg.

As set forth above, by using a NK1-antagonist in combination with neostigmine, it is possible to treat a patient suffering from MG or a myasthenic syndrome by maintaining a therapeutically effective neostigmine daily dose with minimal adverse effect.

Thus, in order to assure a sure, safe and concurrent administration of said NK1-antagonist and neostigmine, the present invention provides a fixed-dose combination consisting of a pharmaceutical composition in dosage unit form comprising an effective amount per unit form of said NK1-antagonist and an effective amount per unit form of said neostigmine, in admixture with a pharmaceutical carrier or vehicle.

These NK1-antagonist/neostigmine fixed-dose combinations are illustrated in "The Fourth aspect of the invention" section below.

The Neostigmine Component (b)

Neostigmine is currently indicated for the oral treatment of MG, as neostigmine bromide, in particular in 15-mg tablets for IR administration; and, as parenteral treatment for the reversal of the effects of non-depolarizing neuromuscular blocking agents (NMBAs) after surgery as neostigmine methylsulfate, in 0.5 mg/ml and 1 mg/ml in 10 ml multiple-dose vials.

According to the FDA approved label for oral neostigmine for the treatment of MG, in order to have a more complete response to said treatment, neostigmine bromide oral doses up to 375 mg/day should be administered. However, as set forth above, said doses are not tolerated in most patients.

Higher neostigmine doses than the currently recommended doses should provide further improvement and even a near-to-complete response, i.e., the complete alleviation of symptoms.

According to the present invention, by constantly combining (with a concurrent administration) neostigmine bromide or neostigmine methylsulfate with a NK1-antagonist, said treatment becomes safe, and greatly increased effective oral doses, up to 1500 mg/day, and even more, or parenteral doses up to 240 mg/day, and even higher, up to 500 mg/day by continuous 24 h-infusion, may be attained without appreciable gastrointestinal adverse effects.

Thus, according to the present invention, for the treatment of symptoms of muscle weakness associated with MG and other myasthenic syndromes in a mammalian subject, neostigmine is formulated in unit forms, in an amount per unit form, including forms for any administration route and for titration, equivalent to from 0.03 mg to 500 mg of neostigmine bromide or methylsulfate. The neostigmine daily dose for this treatment in combination with a NK1-antagonist, including any administration route and titration, is equivalent to from 0.2 mg to 1500 mg of neostigmine bromide or neostigmine methylsulfate.

In general, in combination with a NK1-antagonist, a pharmaceutically acceptable salt of neostigmine is administered at a unit dose equivalent to from 0.03 mg/kg to 6.25 mg/kg of neostigmine bromide or neostigmine methylsulfate. This unit dose includes an oral unit form comprising an amount of said neostigmine equivalent to from 0.2 mg to 200 mg of neostigmine bromide and a parenteral unit form comprising an amount of said neostigmine equivalent to from 0.09 mg to 500 mg of neostigmine methylsulfate.

It is hereby specified that, in the particular case of the subcutaneous continuous 24-infusion route, the term "unit dose" is intended as both a unit form and daily dose.

In combination with a NK1-antagonist, neostigmine is administered to a mammal at a unit dose, including titration doses, equivalent to from 0.25 mg/kg to 2.5 mg/kg of body weight of neostigmine bromide by oral route or equivalent to from 0.03 mg/kg to 6.25 mg/kg, normally from 0.03 mg/kg to 4 mg/kg of body weight of neostigmine methylsulfate by parenteral route.

In particular embodiments, the parenterally administered neostigmine unit dose is equivalent to from 0.03 mg/kg to 0.28 mg/kg of neostigmine methylsulfate by intravenous bolus injection and from 0.03 mg/kg to 8.33 mg/kg, normally from 0.2 mg/kg to 4 mg/kg of neostigmine methylsulfate by subcutaneous continuous 24 h-infusion.

More particularly, for the administration by oral route, the neostigmine oral unit dose normally corresponds to a unit form comprising said neostigmine in an amount per unit form equivalent to from 1 mg to 200 mg of neostigmine bromide;

for the administration by subcutaneous, continuous infusion ("24 h-infusion") route, neostigmine is in a parenteral unit dose equivalent to from 0.16 mg/24 hours ("mg/24 h") to 500 mg/24 h of neostigmine methylsulfate; and for the administration by bolus intravenous route, neostigmine is in a unit form (ampoule or vial) comprising a parenteral unit dose corresponding to a unit form comprising a neostigmine amount equivalent to from 0.09 mg/kg to 0.28 mg/kg of neostigmine methylsulfate.

The amount of neostigmine, normally as bromide, in an oral Immediate Release ("IR") unit form ("amount per unit form") will range from 1 mg to 200 mg, normally from 15 mg to 200 mg, advantageously from 17.5 mg to 200 mg, from 35 mg to 200 mg, from 45 mg to 200 mg, from 62.5 mg to 200 mg, from 70 mg to 200 mg, or from 100 mg to 200 mg, depending on safety and tolerability (per day the oral dose is from 15 mg to 1500 mg, and even more, normally from 17.5 mg to 1500 mg, from 17.5 mg to 1125 mg, from 17.5 mg to 750 mg, or from 17.5 mg to 375 mg). One appropriate neostigmine bromide IR-tablet or IR-capsule comprises 3 mg, 8 mg, 15 mg, 17.5 mg, 35 mg, 50 mg, 62.5 mg, 70 mg, 100 mg, or 200 mg of neostigmine bromide.

Thus, the present invention provides appropriate unit forms, normally a pharmaceutical composition in tablets or capsules comprising, as an active ingredient, a pharmaceutically acceptable salt of neostigmine, in an amount per unit form equivalent to from 17.5 mg to 200 mg, from 35 mg to 200 mg, from 50 mg to 200 mg, from 62.5 mg to 200 mg, from 70 mg to 200 mg or from 100 mg to 200 mg of neostigmine bromide, in admixture with a pharmaceutical carrier or vehicle. Said unit forms may be safely administered to a mammalian subject suffering from symptoms of muscle weakness associated with MG and other myasthenic syndromes, constantly and concurrently with a NK1-antagonist. Tablets each comprising a neostigmine pharmaceutically acceptable salt in an amount per tablet equivalent to 17.5 mg, 35 mg, 50 mg, 62.5 mg, 70 mg, 100 mg and 200 mg of neostigmine bromide are particularly appropriate.

Said unit forms are given several times per day at given intervals depending on the patient's response. The normal, maximally effective neostigmine oral daily dose is equivalent to from more than 375 mg to 1200 mg/day, preferably from 450 mg to 1200 mg/day, of neostigmine bromide, but some patients may need more (up to 1500 mg or more) and some may need less.

In particular, such an oral unit form is destined to be administered from two to seven times per day to mammalian subjects, and particularly, humans, dogs, and cats, suffering from conditions or symptoms of muscle weakness associated with MG or other myasthenic syndromes, in combination with a NK1-antagonist.

In the case of administration of high doses, two unit forms may be simultaneously administered from two to seven times per day to said mammalian subjects in combination with a NK1-antagonist. In this case, the unit dose thus administered does not correspond to a unit form.

For the continuous 24-hour/day subcutaneous neostigmine infusion, the maximally effective daily dose in combination with a NK1-antagonist is equivalent to from 0.2 mg (to neonates) daily to 500 mg daily of neostigmine methylsulfate. Said infusion is in unit doses normally corresponding to the 24-hour dose, preferably in unit doses comprising an amount of neostigmine equivalent to from 0.2 mg to 10 mg, from 10 mg to 50 mg, from 50 mg to 100 mg, from 100 mg to 150 mg, from 150 mg to 200 mg, from 200 mg to 250 mg, from 250 mg to 300 mg, from 300 mg to 350 mg, from 350 to 400 mg, from 400 mg to 450 mg or from 450 mg to 500 mg of neostigmine methylsulfate.

When administered by continuous subcutaneous injection, neostigmine methylsulfate is normally administered at single ampoule doses of from 0.09 mg (to neonates) to 500 mg, to be administered once every 24 hours in order to supply a maximally effective daily dose of from 1 mg (neonates) to 500 mg.

A safer administration is assured by combining, in the same oral unit form, a NK1-antagonist, in an amount per oral unit form of from 1 µg to 600 mg; and neostigmine, in an amount per unit form equivalent to from 0.2 mg to 200 mg, normally from 15 mg to 200 mg, advantageously from 17.5 mg to 200 mg of neostigmine bromide.

In combination with a NK1-antagonist, the effective neostigmine daily dose-range for the treatment of a myasthenic syndrome in a mammal, including parenteral (intravenous, intravenous infusion, subcutaneous, subcutaneous infusion, transcutaneous or intramuscular), oral and other administration means as illustrated in "The formulations" section below, is normally equivalent to from 2 mg to 1500 mg, and even more, of neostigmine bromide or neostigmine methylsulfate.

Preferably, said NK1-antagonist is one of the approved NK1-antagonists described in "The NK1-antagonist" section, in an amount per unit form as described in the same section and said neostigmine is neostigmine bromide or neostigmine methylsulfate.

First Aspect of the Invention

According to a first aspect, the present invention provides a method for safely improving the conditions of mammalian subjects, particularly, humans, dogs, and cats, suffering from symptoms of muscle weakness associated with MG or another myasthenic syndrome, comprising chronically administering to said mammalian subjects a NK1-antagonist in combination with neostigmine.

In particular, the present invention describes a method for safely improving the conditions of a human patient suffering from MG or other myasthenic syndromes and treated with neostigmine by chronically administering to said patient a NK1-antagonist.

Any of the NK1-antagonists illustrated in "The NK1-antagonist" section above may be used for improving the conditions of a mammalian subject suffering from a myasthenic syndrome, in combination with neostigmine at the currently used doses and, in particular, at heretofore intolerable doses and even at very high doses, as illustrated in "The neostigmine Component (b)" section above.

More particularly, the present invention provides a method for safely improving the conditions of a mammal suffering from symptoms of muscle weakness associated with MG and other myasthenic syndromes, which comprises chronically administering to said mammal a NK1-antagonist in combination with neostigmine.

In carrying out the method of the present invention, the daily dose of these NK1-antagonists is at least as high as that preventing or treating nausea and vomiting in pediatric or adult patients undergoing a surgical operation or cancer chemotherapy according to the current protocols for said treatment or prevention. In particular, said daily dose is from 1 µg to 600 mg, normally from 1 mg to 600 mg, or from 1 mg to 300 mg.

The NK1-antagonists allowing safe treatment with neostigmine, in particular at heretofore intolerable doses and even at high doses, are illustrated in "The NK1-antagonist" section.

According to an embodiment,
said NK1-antagonist is selected from the group consisting of aprepitant and pharmaceutically acceptable salts and solvates and prodrugs thereof, rolapitant and pharmaceutically acceptable salts and solvates and prodrugs thereof, netupitant and pharmaceutically acceptable salts and solvates and prodrugs thereof, each at a daily dose illustrated in "The NK1-antagonist" section; and
said neostigmine is selected from the group consisting of pharmaceutically acceptable salts of neostigmine, at a daily dose as illustrated above in "The neostigmine Component (b)" section.

Preferably, said NK1-antagonist is selected from the group consisting of aprepitant and pharmaceutically acceptable salts and solvates thereof, at a daily dose equivalent to from 10 mg to 250 mg of aprepitant; fosaprepitant and pharmaceutically acceptable salts and solvates thereof, at a daily dose equivalent to from 10 mg to 250 mg of aprepitant; rolapitant and pharmaceutically acceptable salts and solvates thereof, at a daily dose equivalent to from 15 mg to 270 mg of rolapitant, netupitant and pharmaceutically acceptable salts and solvates thereof, at a daily dose equivalent to from 300 mg to 600 mg; netupitant-300/palonosetron-0.5 once a day; and fosnetupitant-235/palonosetron-0.25 once a day.

The above daily doses of the above NK1-antagonists allow the safe administration to a mammal of currently used neostigmine daily doses and even of high and very high neostigmine daily doses.

In particular, the above daily doses of said NK1-antagonist allow the safe treatment of adult human patients suffering from MG or other myasthenic syndromes with a neostigmine oral maximally effective daily dose equivalent to from 375 mg to 1500 mg, preferably from 450 mg to 1500 mg; or from 375 mg to 1200 mg, preferably from 450 mg to 1200 mg of neostigmine bromide.

The above daily dose of NK1 antagonists also allows the safe administration to a mammalian subject of parenteral doses of neostigmine, normally as methylsulfate.

For example, aprepitant, at a daily dose of from 10 mg to 250 mg, allows the safe, continuous 24-hour/day subcutaneous neostigmine infusion, at a maximally effective neostigmine daily dose equivalent to a range selected from the group consisting of from 10 mg to 500 mg, from 30 mg to 500 mg, from 120 mg to 500 mg, from 30 mg to 400 mg, from 120 mg to 400 mg, and from 120 mg to 240 mg of neostigmine methylsulfate.

For said treatment, said NK1-antagonist is formulated in a pharmaceutical composition in dosage unit form comprising an effective amount per unit form of said NK1-antagonist, normally from 1 µg to 600 mg, in admixture with a pharmaceutical carrier or vehicle, as illustrated in "The NK1-antagonist Component (a)" section.

Preferably, said NK1-antagonist active ingredient of said pharmaceutical composition is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg; netupitant-300/palonosetron-0.5; and fosnetupitant-235/palonosetron-0.25.

Said NK1-antagonist and said neostigmine may also be co-formulated in a pharmaceutical composition, in admixture with a pharmaceutical carrier or vehicle as illustrated in the "Fourth aspect of the invention" below.

Second Aspect of the Invention

According to a second aspect, the invention provides a NK1-antagonist, for use for the safe treatment of mammalian subjects, and particularly, humans, dogs, and cats, suffering from conditions or symptoms of muscle weakness associated with MG or other myasthenic syndromes, in combination with neostigmine. Such a treatment safely improves said conditions or symptoms.

Any NK1-antagonist, in particular those that are shown to be effective for the prevention or treatment of chemotherapy-induced nausea and vomiting may be used, in a combination, including fixed-dose combinations, with neostigmine according to this aspect of the present invention. Preferably, said NK1-antagonists are those approved for the prevention or treatment of chemotherapy-induced nausea and vomiting.

For its use, said NK1-antagonist is formulated in a pharmaceutical or veterinary composition in dosage unit form comprising an effective amount per unit form of said NK1-antagonist, in admixture with a pharmaceutical carrier or vehicle.

The amounts per unit form of said NK1-antagonists and the daily doses to be administered to a mammal such as a cat or a dog, or a human patient suffering from symptoms of muscle weakness associated with MG or another myasthenic syndrome in combination with neostigmine are described in "The NK1-antagonist" section.

In particular, the NK1-antagonist is in a pharmaceutical or veterinary composition comprising said NK1-antagonist in an effective amount per unit form of from 1 µg to 600 mg to be normally administered to a mammalian subject once a day in combination with neostigmine, also in a pharmaceutical or veterinary composition in dosage unit form comprising an effective amount per unit form of said neostigmine.

Preferably, said NK1-antagonist active ingredient of said pharmaceutical composition is selected from the group consisting of aprepitant and pharmaceutically acceptable salts and solvates thereof, in an amount per unit form equivalent to from 10 mg to 250 mg of aprepitant; fosaprepitant and pharmaceutically acceptable salts and solvates thereof, in an amount per unit form equivalent to from 10 mg to 250 mg of aprepitant; rolapitant and pharmaceutically acceptable salts and solvates thereof, in an amount per unit form equivalent to from 15 mg to 270 mg of rolapitant; netupitant and pharmaceutically acceptable salts and solvates thereof, in an amount per unit form equivalent to from 300 mg to 600 mg; netupitant-300/palonosetron-0.5; and fosnetupitant-235/palonosetron-0.25.

Said composition is for use for safely improving the conditions or symptoms of muscle weakness associated with mammalian subjects, and particularly, humans, dogs, and cats, suffering from MG or other myasthenic syndromes, in combination with neostigmine.

For this treatment in combination with said NK1-antagonist composition, neostigmine is formulated in unit forms, in an amount per unit form, including forms for any administration route and for titration, equivalent to from 0.03 mg to 500 mg of neostigmine bromide or methylsulfate. The neostigmine daily dose for this treatment in combination with a NK1-antagonist, including any administration route and titration, is equivalent to from 0.2 mg to 1500 mg of neostigmine bromide or neostigmine methylsulfate.

Said composition provides a safe treatment for MG or other myasthenic syndromes, in combination, for example, with neostigmine daily oral doses equivalent to from 15 mg to 1500 mg, especially of maximally effective daily oral doses of from 375 mg to 1500 mg, normally from 375 mg to 1200 mg or from 450 mg to 1200 mg of neostigmine bromide.

Said composition also provides for the safe administration to a mammalian subject of parenteral doses of neostigmine, normally as methylsulfate, for example a continuous 24-hour/day subcutaneous neostigmine infusion, at a maximally effective daily dose equivalent to from 10 mg to 500 mg, advantageously from 30 mg to 400 mg, normally from 120 mg to 240 mg of neostigmine methylsulfate.

For said use, the daily dose of these NK1-antagonists is at least as high as that preventing or treating nausea and vomiting in pediatric or adult patients undergoing a surgical operation or cancer chemotherapy according to the current protocols for said treatment or prevention. In particular, said daily dose is from 1 µg to 600 mg, normally from 1 mg to 600 mg, or from 1 mg to 300 mg.

Among the above NK1-antagonists to be used in combination, including fixed-dose combinations, with neostigmine, aprepitant and pharmaceutically acceptable salts or solvate or prodrugs thereof, rolapitant and pharmaceutically acceptable salts or solvates thereof, netupitant and pharmaceutically acceptable salts and solvates and prodrugs thereof are particularly advantageous.

The above daily doses of the above NK1-antagonists allow the safe administration of currently used neostigmine daily doses and even of high and very high neostigmine daily doses.

In particular, the above daily doses of said NK1-antagonist allow the safe treatment of adult patients suffering from MG or other myasthenic syndromes with, for example, a neostigmine oral daily maximally effective dose equivalent to from 375 mg to 1500 mg, normally from 375 mg to 1200 mg or from 450 mg to 1200 mg of neostigmine bromide.

The above daily dose of NK1 antagonists also allows the safe administration to a mammalian subject of parenteral doses of neostigmine, normally as methylsulfate.

For example, aprepitant, at a daily dose of from 10 mg to 250 mg, allows a safe, continuous 24-hour/day subcutaneous neostigmine infusion at an effective daily dose equivalent to a range selected from the group consisting of from 10 mg to 500 mg, from 30 mg to 500 mg, from 120 mg to 500 mg, from 30 mg to 400 mg, from 120 mg to 400 mg, and from 120 mg to 240 mg, of neostigmine methylsulfate.

More particularly, in said combination, said NK1-antagonist is selected from the group consisting of aprepitant and pharmaceutically acceptable salts and solvates thereof, at a daily dose equivalent to from 10 mg to 250 mg of aprepitant; fosaprepitant and pharmaceutically acceptable salts and solvates thereof, at a daily dose equivalent to from 10 mg to 250 mg of aprepitant; rolapitant and pharmaceutically acceptable salts and solvates thereof, at a daily dose equivalent to from 15 mg to 270 mg of rolapitant, netupitant and pharmaceutically acceptable salts and solvates thereof, at a daily dose equivalent to from 300 mg to 600 mg; netupitant-300/palonosetron-0.5; and fosnetupitant-235/palonosetron-0.25.

Said NK1-antagonist and said neostigmine may also be co-formulated in a pharmaceutical composition, in admixture with a pharmaceutical carrier or vehicle as illustrate herein below, in "The fourth aspect of the invention".

Third Aspect of the Invention

According to a third aspect, the invention provides the use of a NK1-antagonist for the preparation of a medicament for the treatment of mammalian subjects, in particular humans, dogs, and cats, suffering from conditions or symptoms of muscle weakness associated with MG or other myasthenic syndromes, in combination with neostigmine. Such a treatment safely improves said conditions or symptoms.

This medicament for the treatment of symptoms of muscle weakness associated with MG and other myasthenic syndromes comprises a NK1-antagonist formulated in a pharmaceutical or veterinary composition in dosage unit form wherein said NK1-antagonist is in admixture with a pharmaceutical carrier or vehicle, to be administered, concurrently or sequentially, in combination with neostigmine.

In said pharmaceutical or veterinary composition for said treatment, said NK1-antagonist is in admixture with a pharmaceutical carrier and formulated in unit forms for oral, intravenous, transcutaneous, or transdermal administration, as described in "The formulations" section below.

According to this third aspect of the present invention, any of the NK1-antagonists described in "The NK1-antagonist Component (a)" section may be used as an active ingredient of said pharmaceutical or veterinary composition indicated for said treatment, in combination with neostigmine doses as described in "The neostigmine Component (b)" section.

According to an embodiment of this third aspect of the invention, said medicament is a pharmaceutical or veterinary composition in dosage unit form comprising, as an active ingredient, said NK1-antagonist, in an amount per unit form of from 1 µg to 600 mg, in admixture with a pharmaceutical carrier or vehicle.

Said medicament, in the above dose per unit form is destined to be administered to said mammalian subject at a daily dose of from 1 µg to 600 mg, in combination with an effective daily dose of neostigmine.

Among the above NK1-antagonists to be used in combination, including fixed-dose combinations, with neostigmine, aprepitant and pharmaceutically acceptable salts and solvates and prodrugs thereof, rolapitant and pharmaceutically acceptable salts and solvates thereof, netupitant and pharmaceutically acceptable salts and solvates and prodrugs thereof are particularly advantageous.

In particular, the medicament according to this third aspect of the invention includes a pharmaceutical or veterinary composition comprising a NK1-antagonist active ingredient selected from the group consisting of aprepitant and pharmaceutically acceptable salts and solvates thereof, in an amount per unit form equivalent to from 10 mg to 250 mg of aprepitant; fosaprepitant and pharmaceutically acceptable salts and solvates thereof, in an amount per unit form equivalent to from 10 mg to 250 mg of aprepitant; rolapitant and pharmaceutically acceptable salts and solvates thereof, in an amount per unit form equivalent to from 15 mg to 270 mg of rolapitant; netupitant and pharmaceutically acceptable salts and solvates thereof, in an amount per unit form equivalent to from 300 mg to 600 mg; netupitant-300/palonosetron-0.5; and fosnetupitant-235/palonosetron-0.25.

The pharmaceutical compositions of the present invention are formulated in unit form with the classic excipients suitable for different ways of administration. Particularly advantageous are the formulations in the form of tablets, multi-score tablets, coated tablets, orally disintegrating tablets, extended release tablets, hard or soft capsules, extended-release capsules, patches for transdermal administration, liquid oral solutions, syrups or suspensions in a predetermined unit form, and vials for the intravenous or subcutaneous administration.

The aforementioned pharmaceutical composition comprising said NK1-antagonist, in the aforementioned amounts per unit form, is administered to a patient suffering from MG or another myasthenic syndrome in combination with neostigmine, also in a pharmaceutical composition in dosage unit form, comprising an effective amount of neostigmine in admixture with a pharmaceutical carrier. Said effective amounts, in unit forms for oral, intravenous, or subcutaneous for continuous infusion administration as well as the neostigmine daily doses, are illustrated in "The neostigmine Component (b)" section.

Normally, said effective amount per unit form for oral administration is in the range of from 0.2 mg to 200 mg, preferably from 17.5 mg to 200 mg. According to a preferred embodiment, said neostigmine is neostigmine bromide. Said effective amount per unit form for continuous subcutaneous infusion administration is from 10 mg to 500 mg, preferably from 60 mg to 240 mg. According to a preferred embodiment, said neostigmine for continuous subcutaneous infusion is neostigmine methylsulfate.

In said combination, said NK1-antagonist is preferably selected from the group consisting of aprepitant and pharmaceutically acceptable salts and solvates thereof, administered at a daily dose equivalent to from 10 mg to 250 mg of aprepitant; fosaprepitant and pharmaceutically acceptable salts and solvates thereof, administered at a daily dose equivalent to from 10 mg to 250 mg of aprepitant; rolapitant and pharmaceutically acceptable salts and solvates thereof, administered at a daily dose equivalent to from 15 mg to 270 mg of rolapitant; netupitant and pharmaceutically acceptable salts and solvates thereof, administered at a daily dose equivalent to from 300 mg to 600 mg of netupitant; netupitant-300/palonosetron-0.5, administered once a day; and fosnetupitant-235/palonosetron-0.25, administered once a day.

According to this third aspect of the present invention, said medicament is destined to be administered to said mammalian subject, at the above daily dose, in combination with neostigmine. Preferably, said neostigmine is neostigmine bromide for oral administration or neostigmine methylsulfate for parenteral administration.

In the treatment of symptoms of muscle weakness associated with MG and other myasthenic syndromes, the NK1-antagonist and the neostigmine are used in combination and the two active components may be co-administered simultaneously or sequentially, or in a fixed dose combination comprising a pharmaceutical composition comprising the NK1-antagonist and neostigmine, in admixture with a pharmaceutically acceptable carrier or vehicle.

As mentioned above, the NK1-antagonist Component (a) and the neostigmine Component (b) can be administered separately or together in any conventional oral or parenteral dosage unit form such as capsule, tablet, powder, sachet, suspension, solution, or transdermal device. The amount of NK1-antagonist per oral unit form in preferred embodiments will be in the range of from 1 µg to 600 mg. The amount of neostigmine per unit form in preferred embodiments will be in the range of from 1 mg to 200 mg, normally from 17.5 mg to 200 mg.

In the case of separate (concurrent or sequential) administration of said NK1-antagonist, in an effective amount per unit form, and of said neostigmine, in an effective amount per unit form, each of them can be packaged in a kit comprising said NK1-antagonist, in admixture with a pharmaceutical carrier or vehicle, in a container; and said neostigmine, in admixture with a pharmaceutical carrier or vehicle, in another, separate container.

For the concurrent administration of said NK1-antagonist and of said neostigmine, the two active principles can be formulated together and with a pharmaceutical carrier or vehicle, in a pharmaceutical composition.

Accordingly, the present invention provides the use of a NK1-antagonist for the preparation of a medicament for the treatment of symptoms of muscle weakness associated with MG and other myasthenic syndromes in combination with neostigmine, said medicament including a pharmaceutical composition in dosage unit form comprising said NK1-antagonist and said neostigmine pharmaceutically acceptable salt, in admixture with a pharmaceutical carrier or vehicle.

Fourth Aspect of the Invention

According to a fourth aspect of the present invention, the pharmaceutical composition comprising a NK1-antagonist may contain another active ingredient, in particular neostigmine, co-formulated with said NK1-antagonist, in admixture with a pharmaceutical carrier or vehicle.

Thus, the present invention further provides a fixed-dose combination including a pharmaceutical or veterinary composition in dosage unit form comprising, as active ingredients, Component (a): a NK1-antagonist; and Component (b): neostigmine, in admixture with a pharmaceutical carrier or vehicle.

Normally, in said composition, the NK1-antagonist Component (a) is present in an amount per unit form of from 1 µg to 600 mg and the neostigmine Component (b) for oral administration is present in an amount equivalent to from 0.2 mg to 200 mg, normally to from 17.5 mg to 200 mg of neostigmine bromide or for subcutaneous 24-hour continuous administration is present in an amount equivalent to 10 mg to 500 mg, or 30 mg to 400 mg, preferably 60 mg to 240 mg of neostigmine methylsulfate.

Said fixed-dose combination is useful for the treatment of MG and other myasthenic disorders in a mammal such as a cat, a dog or a human being. Said treatment safely provides said mammal with a NK1-antagonist dose of from 1 µg to 600 mg and a single neostigmine dose equivalent to from 0.2 mg to 200 mg of neostigmine bromide or neostigmine methylsulfate.

When said mammal is a human being, the above fixed-dose combination may be safely used for the treatment of infants, including neonates, and includes neostigmine doses for titration.

Among the above NK1-antagonists to be used in combination, including fixed-dose combinations, with neostigmine, aprepitant and pharmaceutically acceptable salts and solvates and prodrugs thereof, rolapitant and pharmaceutically acceptable salts and solvates thereof, netupitant and pharmaceutically acceptable salts and solvates and prodrugs thereof are particularly advantageous.

According to one embodiment, said NK1-antagonist Component (a) active ingredient is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg of netupitant; netupitant-300/palonosetron-0.5; and fosnetupitant-235/palonosetron-0.25; and said neostigmine pharmaceutically acceptable salt Component (b) is in an amount per unit form equivalent to from 0.2 mg to 200 mg of neostigmine bromide or 10 mg to 240 mg of neostigmine methylsulfate; and the Components are mixed together and with a pharmaceutical carrier or vehicle.

According to a first aspect of this one embodiment, the fixed-dose combination is a pharmaceutical composition in dosage unit form comprising a NK1-antagonist Component (a) selected from the group consisting of aprepitant, in an amount per unit form of from 10 mg to 250 mg; and rolapitant, in an amount per unit form of from 15 mg to 270 mg; and neostigmine bromide Component (b), in an amount per unit form of from 15 mg to 200 mg, from 17.5 mg to 200 mg, from 35 mg to 200 mg, from 50 mg to 200 mg, from 62.5 mg to 200 mg, from 70 mg to 200 mg and from 100 mg to 200 mg, in admixture with a pharmaceutical carrier or vehicle in an oral formulation.

According to a second aspect of this one embodiment, the fixed-dose combination is a pharmaceutical composition in dosage unit form comprising a NK1-antagonist Component (a) selected from the group consisting of aprepitant, in an amount per unit form of from 25 mg to 200 mg; and fosaprepitant dimeglumine, in an amount per unit form of 25 mg to 200 mg; and neostigmine methylsulfate Component (b), in an amount per unit form of from 0.2 mg to 200 mg, from 17.5 mg to 200 mg, from 35 mg to 200 mg, from 50 mg to 200 mg, from 62.5 mg to 200 mg, from 70 mg to 200 mg and from 100 mg to 200 mg, in admixture with a pharmaceutical carrier or vehicle in a parenteral formulation for injection or infusion.

According to a second embodiment, said Component (a) is a mixture of the NK1-antagonist netupitant, in an amount per unit form of 300 mg, and of the 5HT3-antagonist palonosetron hydrochloride, in an amount per unit form equivalent to 0.5 mg of palonosetron base; and said neostigmine Component (b) is neostigmine bromide in an amount per unit form of from 15 mg to 200 mg, from 17.5 mg to 200 mg, from 35 mg to 200 mg, from 50 mg to 200 mg, from 62.5 mg to 200 mg, from 70 mg to 200 mg and from 100 mg to 200 mg; and the Components are mixed together and with a pharmaceutical carrier or vehicle for oral administration.

According to a third embodiment, said Component (a) is a mixture of the NK1-antagonist fosnetupitant, in an amount per unit form of 235 mg, and of the 5HT3-antagonist palonosetron hydrochloride, in an amount per unit form equivalent to 0.25 mg of palonosetron base; and said neostigmine Component (b) is neostigmine methylsulfate in an amount per unit form of from 0.2 mg to 200 mg, from 17.5 mg to 200 mg, from 35 mg to 200 mg, from 50 mg to 200 mg, from 62.5 mg to 200 mg, from 70 mg to 200 mg and from 100 mg to 200 mg; and the Components are mixed together and with a pharmaceutical carrier or vehicle for parenteral administration or for reconstitution in a solution for parenteral, normally intravenous, administration.

In the above NK1-antagonist/neostigmine fixed dose combinations, the above-illustrated pharmaceutical compositions in dosage unit form are preferably administered to a pediatric or adult patient suffering from symptoms of muscle weakness associated with MG or another myasthenic syndrome to provide a neostigmine oral daily dose equivalent to from 1 mg to 1500 mg, and even more, normally from 15 mg to 1200 mg, from 17.5 mg to 1200 mg, from 270 mg to 1200 mg, from 375 mg to 1200 mg, preferably from 450 mg to 1200 mg of neostigmine bromide or for continuous subcutaneous infusion from 10 mg to 500 mg, or 30 mg to 500 mg, or 60 mg to 240 mg of neostigmine methylsulfate.

The Formulations

For the use in the treatment of symptoms of muscle weakness associated with MG and other myasthenic syndromes in combination with neostigmine, the NK1-antagonist is formulated in a pharmaceutical composition in dosage unit form, wherein said NK1-antagonist is in admixture with a pharmaceutical carrier or vehicle. For said treatment, also neostigmine is formulated in a pharmaceutical composition in dosage unit form, wherein said neostigmine is in admixture with a pharmaceutical carrier or vehicle.

These unit forms are manufactured according to conventional technologies. Particularly advantageous are the formulations in the form of tablets, multi-score tablets, multilayer tablets, coated tables, orally disintegrating tablets, extended release tablets, hard or soft capsules, multi-compartment capsules, extended-release capsules, patches for transdermal administration, liquid oral solutions, syrups or suspensions in a predetermined unit form, apparatus for intravenous infusion, and vials for the intravenous or subcutaneous administration.

As set forth above, the pharmaceutical compositions are formulated in admixture with a pharmaceutical carrier or vehicle for any administration route. For example, said pharmaceutical compositions are in a pharmaceutical dosage unit form for oral, intravenous (including infusion), intramuscular, intranasal, intraperitoneal, subcutaneous, transdermal, or rectal administration.

"Transdermal drug delivery system" (TDDS) provides transdermal delivery using transdermal drug formulations and transdermal patches incorporating such transdermal drug formulations. For example, the transdermal drug delivery system may include a composition in form of a patch, a cream, a gel, a lotion or a paste comprising a NK1-antagonist, neostigmine or both the active ingredients.

Said unit forms are manufactured according to conventional technologies, normally as pharmaceutical compositions formulated with the classic excipients suitable for different ways of administration. Particularly advantageous are the formulations in the form of tablets, multi-score tablets, multi-layer tablets, coated tables, orally disintegrating tablets, extended release tablets, hard or soft capsules, multi-compartment capsules, extended-release capsules, patches for transdermal administration, liquid oral solutions, syrups or suspensions in a predetermined unit form, apparatus for intravenous infusion, and vials for the intravenous or subcutaneous administration.

Said oral forms may be tablets coated with sucrose or with various polymers or, alternatively, the tablets can be manufactured by using carriers such as acrylic and methacrylic acid polymers and copolymers; cellulose derivatives such as hydroxypropylethylcellulose; or other appropriate materials, to have a prolonged or delayed activity by progressively releasing a predetermined quantity of NK1-antagonist or of neostigmine, or of both the active ingredients. The oral formulations can also be in form of capsules allowing the extended release of the NK1-antagonist, or of neostigmine, or of both the active ingredients.

The unit forms may be formulated in tablets in which Component (b) is in Extended Release ("ER")-formulation, for example in admixture with hydroxypropyl methyl cellulose or in a film-coated microgranule. Carriers and vehicles for ER tablets include retardant materials such as acrylic and methacrylic acid polymers and copolymers; the aforementioned cellulose derivatives such as hydroxypropylmethylcellulose, hydroxyethylcellulose, hydroxypropylethylcellulose, hydroxypropylcellulose, methylcellulose, ethylcellulose, or sodium carboxymethylcellulose; gums; waxes; glycerides or aliphatic alcohols or a mixture thereof.

In the combination of the present invention, each unit form may also be a vial containing the pharmaceutical composition a solution, an emulsion, a powder for reconstitution or also an apparatus for continuous infusion of a solution or an emulsion, wherein the active ingredient is dissolved in or mixed with a pharmaceutical carrier for parenteral use.

The pharmaceutical compositions may also be formulated in a TDDS, such as a patch formulation wherein the active ingredient or the mixture of the active ingredients, for example in a matrix, may comprise adjuvants such as D-sorbitol, gelatin, kaolin, methyl paraben, polysorbate 80, propylene glycol, propyl paraben, povidone, sodium carboxymethylcellulose, sodium polyacrylate, tartaric acid, titanium dioxide, and purified water. A patch formulation may also contain skin permeability enhancer such as lactate esters (e.g., lauryl lactate), triacetin or diethylene glycol monoethyl ether.

In the above pharmaceutical compositions, the preferred NK1-antagonist active ingredient is selected from the group consisting of aprepitant and pharmaceutically acceptable salts and solvates and prodrugs thereof, rolapitant and pharmaceutically acceptable salts and solvates thereof, and netupitant and pharmaceutically acceptable salts and solvates and prodrugs thereof, preferably aprepitant, fosaprepitant, rolapitant, netupitant-300/palonosetron-0.5; or fosnetupitant-235/palonosetron-0.25, and the preferred neostigmine is neostigmine bromide or neostigmine methylsulfate.

Thus, for example, a pharmaceutical composition according to the present invention, to be chronically administered in combination with neostigmine, comprises a NK1-antagonist selected from the group consisting of aprepitant and pharmaceutically acceptable salts and solvates and prodrugs thereof, in an amount/unit form equivalent to from 10 mg to 250 mg of aprepitant; rolapitant and pharmaceutically acceptable salts and solvates thereof, in an amount/unit form equivalent to from 30 mg to 270 mg of rolapitant; and netupitant and pharmaceutically acceptable salts and solvates and prodrugs thereof, in an amount/unit form equivalent to from 150 mg to 600 mg of netupitant.

When the NK1-antagonist and neostigmine are in a fixed-dose combination for oral administration, the unit form may be a stratified, bi-layer tablet wherein the NK1-antagonist, formulated with a pharmaceutical carrier, normally in IR-formulation, is in one of the layers and neostigmine, formulated with a pharmaceutical carrier, is the other layer, preferably in ER-formulation. Similarly, the NK1-antagonist and neostigmine active ingredients are in a pill containing one of the active ingredients, admixed with a pharmaceutical carrier, in the core and the other active ingredient, admixed with a pharmaceutical carrier, is in the outer part of the pill, the core and the outer part being optionally separated by an inert film or carrier. Analogously, capsules made of two separated parts, one containing Component (a), in IR-formulation and the other containing Component (b), in ER-formulation, may be manufactured.

Especially in the case of mammalian subject such as cats and dogs and of human pediatric or obese human patients, the NK1-antagonist and neostigmine daily dose may be decided on the basis of the body weight.

Thus, for example, aprepitant may be administered at a daily dose of 0.16 mg/kg to 4.2 mg/kg and rolapitant may be administered at a daily dose of 0.25 mg/kg to 4.5 mg/kg. The above doses are preferably administered by oral route.

Neostigmine may be administered at a single oral dose equivalent to from 0.25 mg/kg to 2.5 mg/kg of body weight of neostigmine bromide; at a single parenteral dose equivalent to from 0.03 mg/kg to 6.25 mg/kg, normally from 0.03 mg/kg to 4 mg/kg, of body weight of neostigmine methylsulfate.

Kits

The present invention also provides a kit or package containing a medicament, a pharmaceutical combination, or a pharmaceutical composition as described herein, accompanied by instructions for use of the same in the treatment of symptoms of muscle weakness associated with myasthenia gravis or another myasthenic syndrome in a mammalian subject in need thereof.

In one embodiment, a kit of the present invention is a kit comprising a combination of a NK1-antagonist and neostigmine, formulated together in a pharmaceutical composition, in admixture with a pharmaceutical carrier or vehicle; and instructions for use of the same for treatment of symptoms of muscle weakness associated with myasthenia gravis or another myasthenic syndrome in a mammalian subject in need thereof.

In another embodiment, a kit of the present invention is a kit comprising pharmaceutical composition (a) comprising a NK1-antagonist and pharmaceutical composition (b) comprising neostigmine; and instructions for use of the same for treatment of symptoms of muscle weakness associated with myasthenia gravis or another myasthenic syndrome in a mammalian subject in need thereof.

The foregoing detailed description has been given for illustration purposes only, especially for purposes of clarity of understanding. The description is not meant to be construed in a limiting sense. It will be apparent to those skilled in the art that certain changes and modifications of the disclosed embodiments as well as alternative embodiments may be practiced without departing from the spirit and scope of the invention. It is contemplated that the appended claims will cover any such modifications or embodiments that fall within the scope of the invention.

EXAMPLES

The ability of the NK1-antagonists for preventing the adverse effects of orally administered neostigmine bromide in humans is tested.

A Phase I study is conducted in human subjects receiving a single oral dose of neostigmine bromide with or without a single oral dose of aprepitant hydrochloride dihydrate, as a representative NK1-antagonist. The study is a single center, single-blind, placebo-controlled study.

The objective of the study is to demonstrate that aprepitant safely attenuates the gastro-intestinal side effects of neostigmine given in doses shown to be effective for the treatment of Myasthenia Gravis (Prostigmin® Prescribing Information).

To be enrolled in the study, participants are to meet the following inclusion/exclusion criteria:
Key Inclusion Criteria
1. Male or female volunteers between the ages of 18 and 60 years inclusive are required to be in good health, to refrain from consuming xanthine, quinine and caffeine containing beverages, and to refrain from prolonged intensive physical exercise during the study conduct.
2. Subjects are to sign an informed consent form indicating that they understand the purpose of and procedures for the study and that they are willing to participate in the study and comply with the study procedures and restrictions.
3. Subjects had to be in good health according to their medical history including personal and family psychiatric history, physical examination, ECG, vital signs, and laboratory tests. A subject with a medical abnormality could be included only if the investigator or designee considers that the abnormality does not introduce significant additional risk to the subject's health or interfere with study objectives.
4. Subjects had to be able to swallow multiple pills simultaneously.
Key Exclusion Criteria
1. Any clinically relevant acute or chronic disease which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of drugs.
3. History of substance abuse, known drug addiction, or positive test for drugs of abuse or alcohol.
4. History of drug or other significant allergy.
5. ECG changes including QT interval prolongation and congenital long QT syndrome. Electrolyte abnormalities (e.g., hypokalemia or hypomagnesemia), congestive heart failure, bradyarrhythmias or other conditions that lead to QT prolongation;
6. Treatment with centrally active drugs or those affecting peripheral cholinergic transmission within 3 months of study entry.
7. Smokers (except subjects who stopped smoking 1 year or more before enrollment in the Study).
8. Excessive daily consumption of xanthines containing drinks (i.e. >500 mg/day of caffeine).
9. Intake of an investigational drug within 30 days of study entry.

Following enrollment in the study, participants will receive single increasing oral doses of neostigmine, given once daily in the morning. Once a subject reaches his/her first intolerable dose ("FID-1"), upward dose escalation is discontinued. FID is defined as:
(a) one episode of vomiting; or
(b) two episodes of retching; or
(c) one episode of severe nausea (Grade 3; defined as nausea interfering with activities of daily living or inadequate oral caloric or fluid intake; tube feeding, total parenteral nutrition or hospitalization indicated) lasting more than 1 hour; or
(d) one episode of moderate diarrhea (Grade 2); defined as 4-6 stools more than at baseline); or
(e) three (3) consecutive episodes at every 4 hour ratings of moderate nausea (Grade 2; defined as subjectively symptomatic, but not interfering with activities of daily living).

When a subject reaches FID-1 on neostigmine alone, the subject is washed out for 2 to 7 days, and then receives their first intolerable dose (FID) of neostigmine plus a single oral dose of aprepitant, (in doses of aprepitant up to 125 mg as necessary to prevent or attenuate dose-limiting gastro-intestinal adverse events) or aprepitant placebo.

On each study day, subjects are followed up for up to 8 hours for AEs, vital signs, and ECGs. In addition, a laboratory panel at screening and at the end of the study is taken.

The co-administration of an oral effective dose aprepitant with neostigmine prevents or attenuates the occurrence of gastro-intestinal AEs with neostigmine given in doses at least as high as or much higher than the currently recommended efficacious dose of neostigmine for the treatment of myasthenia gravis.

REFERENCES

Abicht et al, 2003 updated in 2014: Abicht A, Müller J S, Lochmüller H. "Congenital Myasthenic Syndromes". In: Pagon R A, Adam M P, Ardinger H H, Wallace S E, Amemiya A, Bean U H, Bird T D, Ledbetter N, Mefford H C, Smith R J H, Stephens K, editors. GeneReviews® [Internet]. Seattle (Wash.): University of Washington, Seattle; 1993-2016. 2003 May 9 [updated 2016 Jul. 14].
Drachman, 2016: Drachman D B. "Myasthenia Gravis". Semin Neurol. 2016; 36:419-424. Epub 2016 Sep. 23.
Engel, 2012: Engel A G. "Congenital Myasthenic Syndromes in 2012". Curr. Neurol Neurosci Rep, 2012; 12:92-101.
Gotterer and Li, 2016: Gotterer L, Li Y. "Maintenance immunosuppression in myasthenia gravis". J Neurol Sci. 2016; 369:294-302. Epub 2016 Aug. 28.
Howard, 2015: Howard J F. "Clinical Overview of M G. Myasthenia Gravis" Foundation of America; 2015.
Lexell 1997: Lexell J. "Evidence for Nervous System Degeneration with Advancing Age". The Journal of Nutrition, Volume 127, Issue 5, 1 May 1997, Pages 10115-10135, https://doi.Org/10.1093/jn/127.5.1011S.
Makarious et al. 2017: Makarious D, Horwood K, Coward J. I. G. "Myasthenia gravis: An emerging toxicity of immune checkpoint inhibitors". European J Cancer 82 (2017), 128-136.
O'Grady et al, 2016: O'Grady G L, Verschuuren C, Yuen M, Webster R, Menezes M, Fock J M, Pride N, Best H A, Benavides Damm T, Turner C, Lek M, Engel A G, North K N, Clarke N F, MacArthur D G, Kamsteeg E J, Cooper S T. "Variants in SLC18A3, vesicular acetylcholine transporter, cause congenital myasthenic syndrome". Neurology. 2016; 87: 1442-1448. Epub 2016 Sep. 2.

Phillips and Vincent, 2016: Phillips W D, Vincent A. "Pathogenesis of myasthenia gravis: update on disease types, models, and mechanisms". FIOOORes. 2016; 27:5.

Shelton, 2016: Shelton G D. "Myasthenia gravis and congenital myasthenic syndromes in dogs and cats: A history and mini-review". Neuromuscul Disord. 2016; 26: 331-334. Epub 2016 Mar. 10.

Smith and Lee, 2017: Smith S V, Lee A G. "Update on Ocular Myasthenia Gravis". Neurol Clin. 2017; 35: 115-123.

EXEMPLARY ASPECTS

The following is a non-limiting list of exemplary aspects of the invention, presented as a listing of embodiments, which is intended to highlight and illustrate various facets of the invention. In this respect, the invention provides, among other things—

1. A method for safely improving the conditions of a mammal suffering from symptoms of muscle weakness associated with MG or another myasthenic syndrome, comprising chronically administering to said mammal a NK1-antagonist in combination with neostigmine.

2. The method of aspect 1, wherein said neostigmine is neostigmine bromide or neostigmine methylsulfate.

3. The method of aspect 1, wherein said NK1-antagonist is aprepitant or a pharmaceutically acceptable salt or solvate or prodrug thereof.

4. The method of aspect 1, wherein said NK1-antagonist is administered to said mammal at a single oral or subcutaneous dose of from 1 μg to 600 mg/day.

5. The method of aspect 1, wherein said neostigmine in said combination is administered to said mammal at a daily dose, for any administration route and including titration doses, equivalent to from 0.2 mg to 1500 mg of neostigmine bromide or neostigmine methylsulfate.

6. The method of aspect 5, wherein said neostigmine is administered to said mammal at a maximally effective parenteral daily dose, by intravenous 24 h-infusion, equivalent to from 10 mg to 500 mg of neostigmine methylsulfate.

7. The method of aspect 5, wherein said neostigmine is administered to said mammal at a maximally effective oral daily dose equivalent to from 375 mg to 1500 mg of neostigmine bromide.

8. The method according to aspect 1, wherein said neostigmine in said combination is administered to said mammal in a unit form, for any administration route and including titration doses per unit form, comprising said neostigmine in an amount per unit form equivalent to from 0.09 mg to 500 mg of neostigmine bromide or neostigmine methylsulfate.

9. The method of aspect 8, wherein said neostigmine is administered to said mammal in a unit form for continuous subcutaneous infusion comprising said neostigmine in an amount per said unit form equivalent to from 0.09 mg to 500 mg of neostigmine methylsulfate.

10. The method of aspect 8, wherein said neostigmine is administered to said mammal in a unit form for oral administration comprising said neostigmine in an amount per said unit form equivalent to from 15 mg to 200 mg of neostigmine bromide.

11. The method of aspect 3, wherein said prodrug of said aprepitant is fosaprepitant.

12. The method of aspect 1, wherein said mammal is suffering from myasthenia gravis.

13. The method of aspect 12, wherein the mammal is a human, dog or cat.

14. A pharmaceutical combination comprising a NK1-antagonist and neostigmine.

15. A pharmaceutical composition comprising a NK1-antagonist and neostigmine.

16. The composition of aspect 15, further comprising a pharmaceutically acceptable carrier or vehicle.

17. A kit comprising the pharmaceutical combination of aspect 14, or the pharmaceutical composition of aspect 15, and instructions for treatment of symptoms of muscle weakness associated with myasthenia gravis or another myasthenic syndrome.

18. The pharmaceutical combination of aspect 14, or pharmaceutical composition of claim 15, wherein said NK1-antagonist is present at a daily dose of from 1 μg to 600 mg and said neostigmine is present at a daily dose equivalent to from 0.2 mg to 1500 mg of neostigmine bromide or methylsulfate.

What is claimed is:

1. A method for safely improving the conditions of a mammal suffering from symptoms of muscle weakness associated with myasthenia gravis or another myasthenic syndrome, comprising chronically administering to said mammal an NK1-antagonist comprising aprepitant at a daily dose equivalent of from 10 mg to 250 mg or fosaprepitant at a daily dose equivalent of from 10 mg to 250 mg in combination with an oral dose of from 375 mg to 1500 mg of neostigmine bromide.

2. The method of claim 1, wherein said mammal is suffering from myasthenia gravis.

3. The method of claim 2, wherein the mammal is a human.

4. The method of claim 3, wherein said NK1-antagonist is a pharmaceutically acceptable salt of aprepitant or a pharmaceutically acceptable salt of fosaprepitant.

5. A method for safely improving the conditions of a mammal suffering from symptoms of muscle weakness associated with myasthenia gravis or another myasthenic syndrome, comprising chronically administering to said mammal an NK1-antagonist comprising aprepitant at a daily dose equivalent of from 10 mg to 250 mg or fosaprepitant at a daily dose equivalent of from 10 mg to 250 mg in combination with a parenteral daily dose administered by intravenous 24 h infusion, equivalent to from 10 mg to 500 mg of neostigmine methylsulfate.

6. The method of claim 4, wherein the neostigmine is provided in a pharmaceutically acceptable dosage form comprising one or more pharmaceutically acceptable carriers comprising one or more pharmaceutically acceptable polymers wherein the one or more pharmaceutically acceptable polymers facilitate release of the neostigmine from the dosage form.

7. The method of claim 6, wherein the neostigmine and the NK-1 antagonist are administered to the mammal together in a combination dosage form.

8. The method of claim 5, wherein said mammal is suffering from myasthenia gravis.

9. The method of claim 8, wherein the mammal is a human.

10. The method of claim 9, wherein said NK1-antagonist is a pharmaceutically acceptable salt of aprepitant or a pharmaceutically acceptable salt of fosaprepitant.

11. The method of claim 10, wherein the neostigmine is provided in a pharmaceutically acceptable dosage form comprising one or more pharmaceutically acceptable carriers comprising one or more pharmaceutically acceptable polymers wherein the one or more pharmaceutically acceptable polymers facilitate release of the neostigmine from the dosage form.

12. The method of claim 11, wherein the neostigmine and the NK-1 antagonist are administered to the mammal together in a combination dosage form.

13. A method for safely improving the conditions of a mammal suffering from symptoms of muscle weakness associated with myasthenia gravis or another myasthenic syndrome, comprising chronically administering to said mammal an NK1-antagonist comprising aprepitant at a daily dose equivalent of from 10 mg to 250 mg or fosaprepitant at a daily dose equivalent of from 10 mg to 250 mg in combination with an oral dose of from 270 mg to 1200 mg of neostigmine bromide.

14. The method of claim 13, wherein said mammal is suffering from myasthenia gravis.

15. The method of claim 14, wherein the mammal is a human.

16. The method of claim 15, wherein said NK1-antagonist is a pharmaceutically acceptable salt of aprepitant or a pharmaceutically acceptable salt of fosaprepitant.

17. The method of claim 16, wherein the neostigmine is provided in a pharmaceutically acceptable dosage form comprising one or more pharmaceutically acceptable carriers comprising one or more pharmaceutically acceptable polymers wherein the one or more pharmaceutically acceptable polymers facilitate release of the neostigmine from the dosage form.

18. The method of claim 17, wherein the neostigmine and the NK-1 antagonist are administered to the mammal together in a combination dosage form.

19. The method of claim 1 wherein the daily dose equivalent of aprepitant or fosaprepitant is from 25 mg to 200 mg.

* * * * *